(12) United States Patent
Jakob et al.

(10) Patent No.: US 8,394,070 B2
(45) Date of Patent: Mar. 12, 2013

(54) DEVICE FOR BOLUS ADMINISTRATION OF CONTRAST AGENT

(75) Inventors: Laurent Jakob, Bernex-Suisse (CH); Frederic Rivas, Annemasse (FR)

(73) Assignee: Bracco Suisse S.A., Manno (CH)

( * ) Notice: Subject to any disclaimer, the term of this patent is extended or adjusted under 35 U.S.C. 154(b) by 111 days.

(21) Appl. No.: 13/133,572

(22) PCT Filed: Dec. 15, 2009

(86) PCT No.: PCT/EP2009/067151
§ 371 (c)(1),
(2), (4) Date: Jun. 8, 2011

(87) PCT Pub. No.: WO2010/069943
PCT Pub. Date: Jun. 24, 2010

(65) Prior Publication Data
US 2011/0245664 A1    Oct. 6, 2011

(30) Foreign Application Priority Data
Dec. 16, 2008    (EP) ..................................... 08171787

(51) Int. Cl.
*A61M 5/00* (2006.01)
*A61B 6/00* (2006.01)
(52) U.S. Cl. ......... 604/232; 604/193; 604/224; 600/432
(58) Field of Classification Search ............. 604/82–83, 604/85, 187, 191–193, 224, 232; 600/432; 141/311 R
See application file for complete search history.

(56) References Cited

U.S. PATENT DOCUMENTS

| | | | | |
|---|---|---|---|---|
| 4,281,665 A | * | 8/1981 | Gezari | 600/526 |
| 4,826,483 A | * | 5/1989 | Molnar, IV | 604/110 |
| 4,846,794 A | * | 7/1989 | Hertzer | 604/83 |
| 5,053,019 A | | 10/1991 | Duffy | |
| 5,271,928 A | | 12/1993 | Schneider et al. | |
| 5,385,545 A | * | 1/1995 | Kriesel et al. | 604/82 |
| 5,413,774 A | | 5/1995 | Schneider et al. | |
| 5,582,598 A | * | 12/1996 | Chanoch | 604/208 |
| 5,597,549 A | | 1/1997 | Schneider et al. | |
| 5,711,933 A | | 1/1998 | Bichon et al. | |
| 5,827,504 A | | 10/1998 | Yan et al. | |
| 6,333,021 B1 | | 12/2001 | Schneider et al. | |

(Continued)

FOREIGN PATENT DOCUMENTS

WO    2004/069284 A2    8/2004

OTHER PUBLICATIONS

PCT International Search Report and PCT Written Opinion of the International Searching Authority for PCT/EP2009/067151, mail date Apr. 6, 2010.

(Continued)

*Primary Examiner* — Quynh-Nhu H Vu
(74) *Attorney, Agent, or Firm* — M. Caragh Noone

(57) ABSTRACT

A device for administering a liquid preparation comprising a pharmaceutical agent, particularly a contrast agent, in the form of a bolus. The device comprises in particular a core cylinder and an external cylinder, the core cylinder comprising a conduit (107) and a cylindrical reservoir (108) cooperating with a respective plunger (109), wherein the plunger is modified in order to operatively engage with guiding means (300) provided on the external cylinder.

14 Claims, 5 Drawing Sheets

U.S. PATENT DOCUMENTS

| | | | |
|---|---|---|---|
| 6,406,455 B1 * | 6/2002 | Willis et al. | 604/68 |
| 6,712,794 B2 * | 3/2004 | Kust et al. | 604/224 |
| 6,871,087 B1 | 3/2005 | Hughes et al. | |
| 2003/0078546 A1 * | 4/2003 | Jensen | 604/232 |
| 2004/0127858 A1 * | 7/2004 | Bendek et al. | 604/208 |
| 2007/0112308 A1 * | 5/2007 | Kay et al. | 604/187 |
| 2009/0187151 A1 * | 7/2009 | Kleyman et al. | 604/224 |

OTHER PUBLICATIONS

Extended European Search Report for European application No. EP08171787.8, mail date Jul. 28, 2009.

PCT International Preliminary Report on Patentability (Chapter 1 of the PCT) for PCT/EP2009/067151, mail date Jun. 30, 2011.

* cited by examiner

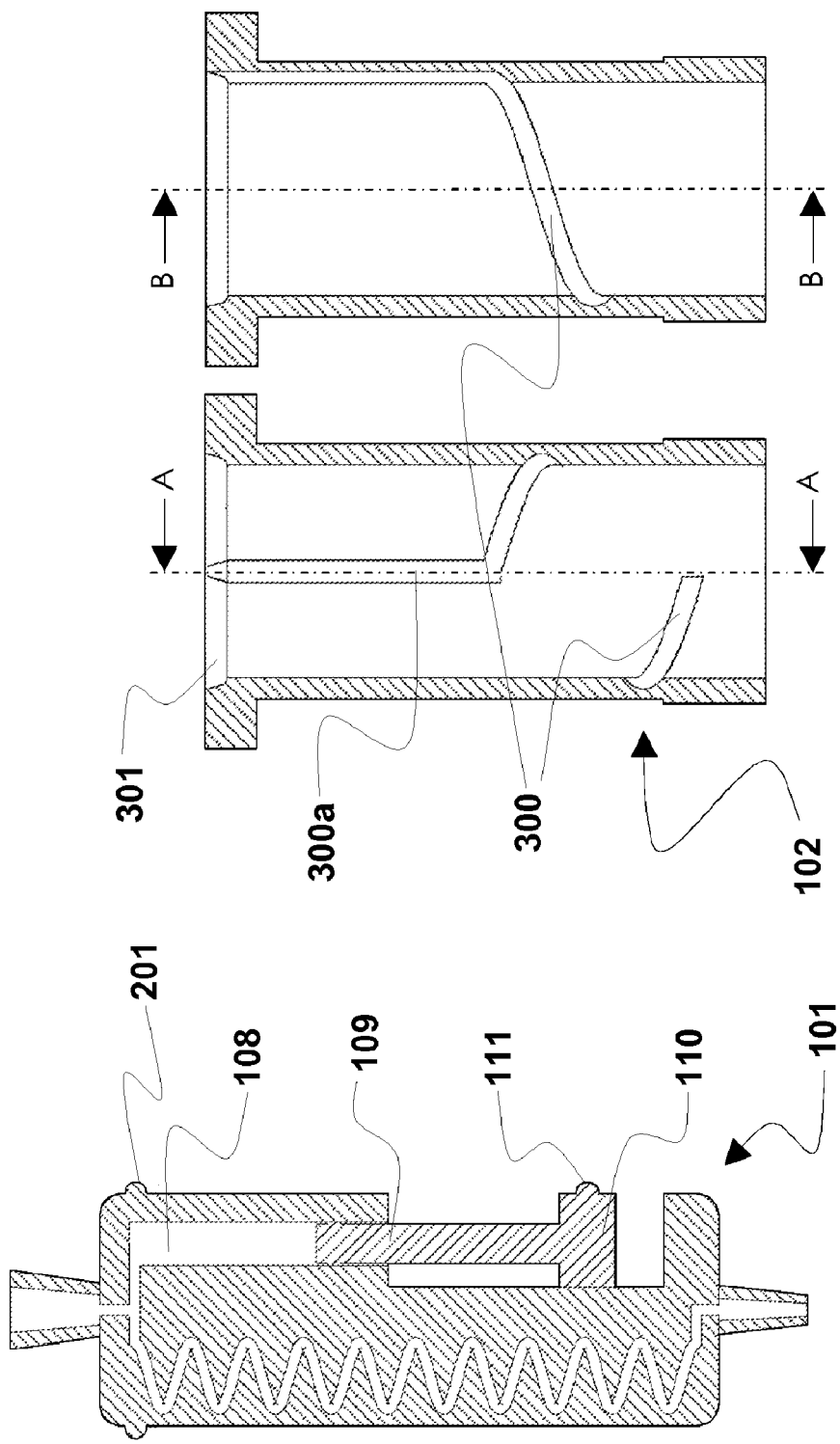

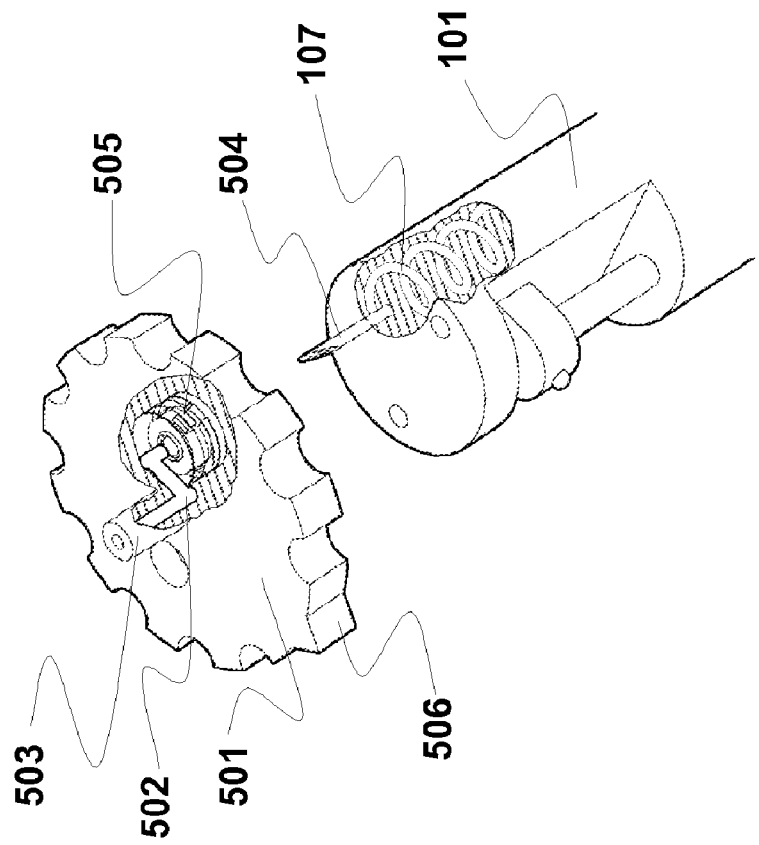
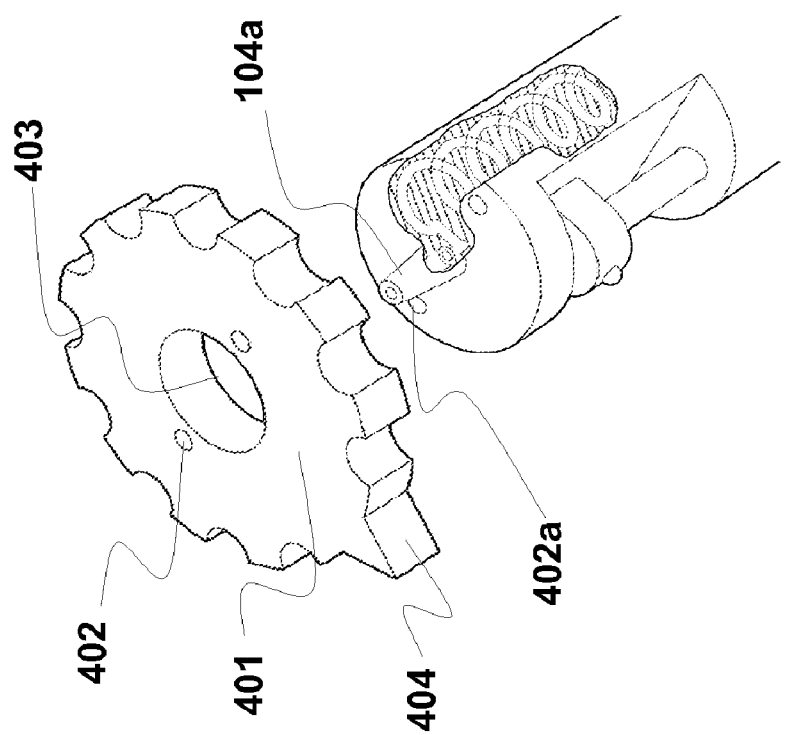

US 8,394,070 B2

DEVICE FOR BOLUS ADMINISTRATION OF CONTRAST AGENT

CROSS-REFERENCE TO RELATED APPLICATIONS

This application is the national stage application of corresponding international application number PCT/EP2009/067151 filed Dec. 15, 2009, which claims priority to and the benefit of European application no. 08171787.8, filed Dec. 16, 2008, all of which are hereby incorporated by reference in their entireties.

TECHNICAL FIELD

The invention relates to a device for administering a liquid preparation comprising a pharmaceutical agent, particularly a contrast agent, in the form of a bolus.

BACKGROUND OF THE INVENTION

The administration by injection of a preparation comprising a pharmaceutical compound is often required to be performed in a relatively short time and with a relatively high local concentration of the pharmaceutical agent. This practice is generally referred to in the field as "bolus" injection. Typically, the term "bolus injection" thus identifies the administration at once (in general within less than few seconds) of a pharmaceutical agent at a high concentration, differently from a gradual administration of the agent (e.g. by means of intravenous infusion).

For instance, in the diagnostic field, liquid preparations of contrast agents (e.g. suspensions of gas-field microvesicles for ultrasound imaging) are often required to be administered as a bolus injection.

Bolus injection is generally achieved by injecting a predetermined volume (the actual bolus) of the desired pharmaceutical liquid preparation followed by a volume of a driving liquid (e.g. saline). According to this technique, it is important, among other things, to precisely determine the volume of the injected bolus and to avoid as much as possible any mixing between the driving liquid and the bolus, as well as any delay between the injection of the bolus volume and the driving liquid.

Several devices and methods have been proposed to collect predetermined volumes of a pharmaceutical preparation and to administer it as a bolus, as disclosed for instance in U.S. Pat. No. 5,053,019.

The Applicant has now devised a new device and system for administering a pharmaceutical preparation as a bolus to a patient.

SUMMARY OF THE INVENTION

According to an aspect thereof, the present invention relates to a device 100 for transferring a volume of a pharmaceutical preparation, said device comprising:
a) an external cylinder 102, comprising:
  i) an inner and an outer longitudinal surface, said inner longitudinal surface comprising guiding means 300; and
  ii) a proximal end 105 and a distal end 106;
b) a core cylinder 101, comprising:
  i) a respective inner and outer longitudinal surface;
  ii) a proximal end 103 and a distal end 104, said proximal and distal ends comprising respective passages 103b and 104b, said passages being in fluid communication with corresponding connecting means 103a and 104a adapted to releasably connect the device with respective injection and/or administration devices:
  iii) a conduit 107, arranged between and in fluid communication with respective passages 103b and 104b; and
  iv) a cylindrical reservoir 108, in fluid communication with said passage 103b and cooperating with a respective plunger 109, said plunger being adapted to operatively engage with the guiding means 300.

Preferably, said guiding means 300 and said plunger 109 are operatively engaged such that a relative rotation of the external cylinder with respect to the core cylinder results in a corresponding longitudinal movement of the plunger 109 along the reservoir 108.

According to a preferred embodiment, said guiding means 300 comprise a groove, preferably of helicoidal form. Preferably, the head of the plunger 109 is modified to comprise a protrusion for engaging with said groove.

According to a preferred embodiment, the external cylinder comprises a graduated scale on the outer surface thereof.

According to another aspect, the invention relates to a system for administering a preparation of a pharmaceutical compound to a patient comprising injecting means, a device as above defined and administration means.

BRIEF DESCRIPTION OF THE DRAWINGS

FIG. 2 represent a cross section of an embodiment of the core cylinder.

FIG. 3 represents A-A and B-B longitudinal cross-sections of an embodiment of an external cylinder.

FIG. 4 represents an embodiment of a core cylinder with retaining means.

FIG. 5 represents an alternative embodiment of a core cylinder with retaining means.

DETAILED DESCRIPTION OF THE INVENTION

Figure 1:
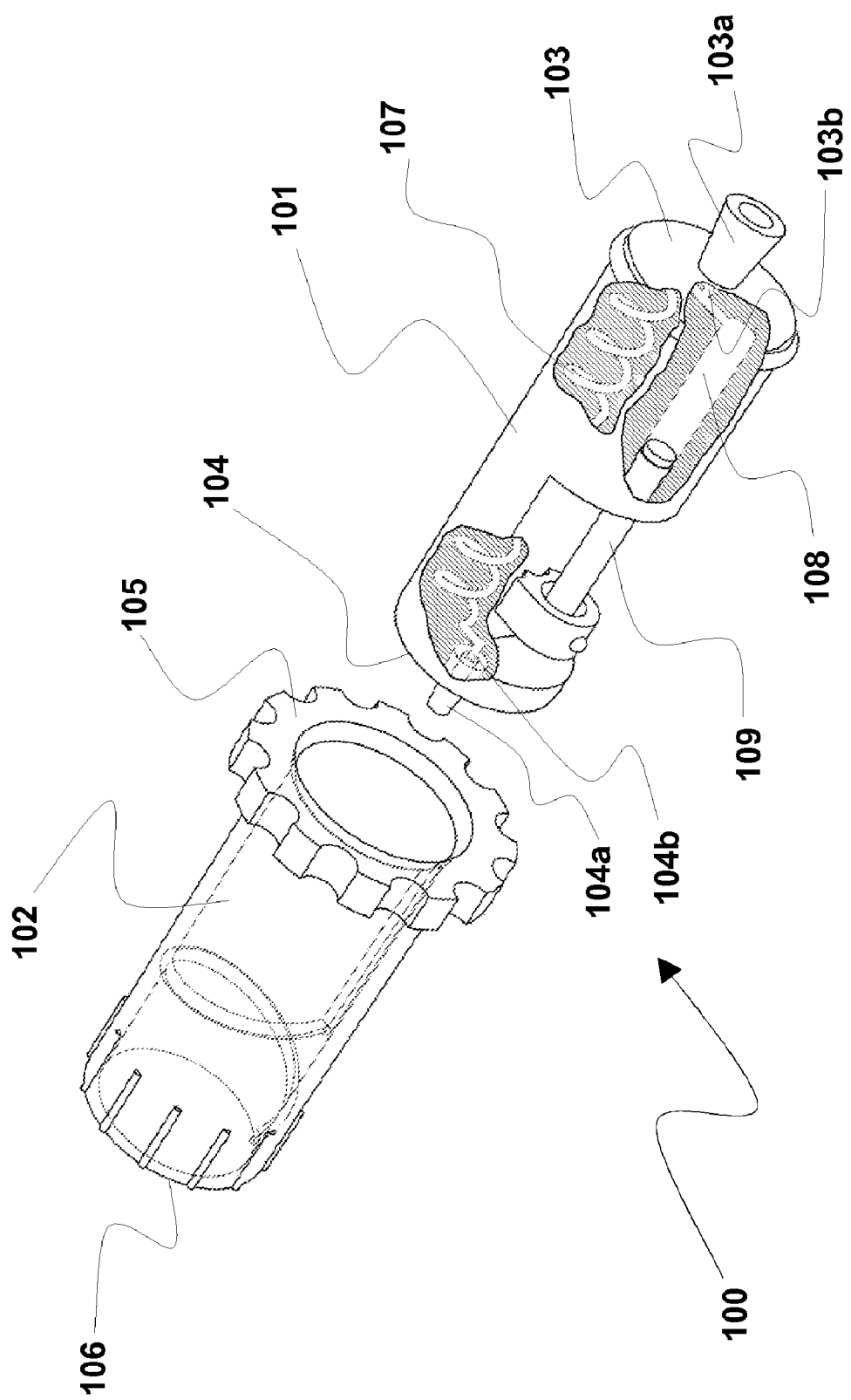
FIG. 1 represents a phantom view of an external cylinder and a partial cut away view of a core cylinder forming a device according to an embodiment of the invention.

As illustrated in FIG. 1, the device 100 comprises a core cylinder 101 and an external cylinder 102, said core and external cylinders comprising respective proximal ends 103 and 105 and distal ends 104 and 106. Proximal and distal ends of the core cylinder comprise respective connecting means 103a and 104a (e.g. a luer lock), to releasably connect the device with suitable respective injection and/or administration devices. As illustrated in detail also in FIG. 2, proximal end 103 further comprises a passage 103b, which is in fluid communication with connection 103a. Similarly, distal end 104 comprises a passage 104b, which is in fluid communication with connection 104a. The core cylinder further comprises a conduit 107, which is in fluid communication with both passages 103b and 104b. The conduit 107 has preferably a relatively small diameter, in order to substantially limit or avoid any mixing of the fluid contained therein with the fluid contained in external containers during injection or withdrawal of liquids. The small diameter of the conduit has also the advantage of limiting or substantially avoiding any undesirable separation of a material suspended in the pharmaceutical preparation. Furthermore, the conduit 107 has preferably a tortuous path, e.g. in the form a spiral, in order to maximize its length within device 100 and thus the volume of liquid contained therein. For instance, the conduit may have an internal diameter of from about 0.5 mm to about 2.0 mm, preferably of from about 0.75 mm to about 1.5 mm, and a length of from about 5 cm to about 200 cm, preferably of from about 20 to about 100 cm. The volume inside the conduit 107 may typically range from about 100 µl to about 1 ml.

The core cylinder 101 also comprises a cylindrical reservoir 108 (independently located, with respect to conduit 107, within the core cylinder) cooperating with a respective plunger 109; the reservoir 108 is in fluid communication with the proximal end's passage 103b. Preferably, in order to avoid undesirable withdrawal of pharmaceutical preparation into the reservoir 108, the volume thereof is selected to be slightly less than the volume of conduit 107.

The inner surface of the external cylinder 102 is preferably dimensioned to exactly mate with the outer surface of the core cylinder 101; in particular, the core and the external cylinder have a cylindrical shape with diameters selected to maintain the respective surfaces of the two cylinders in substantial contact to each other once the two cylinders are coupled.

To allow the upward and downward movement of plunger 109 along reservoir 108, the plunger and the inner surface of the external cylinder are respectively modified to suitably cooperate with each other. For instance, as illustrated in FIGS. 2 and 3, the head 110 of the plunger 109 is provided with a protrusion 111, adapted to engage with a respective helicoidal groove 300 provided on the inner surface of the external cylinder 102. The groove 300 preferably comprises a terminal portion 300a formed along the axis of the external cylinder, to facilitate the insertion of the core cylinder into the external cylinder. Once the device is assembled, i.e. once the core cylinder is inserted into the external cylinder, the relative rotation of the external cylinder with respect to the core cylinder (along respective coincident longitudinal axes) results in a corresponding longitudinal movement of the plunger 109 along the reservoir 108.

The assembling of the device should be such that the core cylinder 101 is allowed to rotate along its longitudinal axis inside the external cylinder, while avoiding any relative longitudinal movement between the two cylinders (to avoid uncontrolled displacement of the plunger). The two cylinders are thus preferably provided with respective blocking means, which cooperate to substantially avoid longitudinal movements of the core cylinder with respect to the external cylinder. For instance, the two cylinders, as illustrated in FIGS. 2 and 3, are provided with cooperating portions 201 (e.g. a rib) and 301 (e.g. a corresponding groove) at their respective proximal ends, to block the further forward longitudinal movement of the core cylinder once it has been inserted inside the external cylinder. Once the core cylinder has been inserted into the external cylinder, with the respective tapered portions 201 and 301 in contact to each other, the distal end of the core cylinder is then preferably connected to retaining means, to prevent a backward longitudinal movement of the core cylinder. As illustrated in FIG. 4, retaining means may have the form of a disk 401. The disk is fixed to the core cylinder by any suitable fixing means, e.g. by means of screws through holes 402 matching with corresponding holes 402a on the top of the distal end of core cylinder. In its simpler form, the disk 401 may have a central opening 403, to allow the passage of connecting means 104a of the core cylinder 101. In an alternative embodiment illustrated FIG. 5, the disk 501 is itself part of the core cylinder 102. According to this embodiment, the disk 501 comprises a passage 502 and connecting means 503 (e.g. a luer lock), to connect the device with suitable respective means for injection. Passage 502 is thus in fluid communication with conduit 107, located in the body of the core cylinder 101, through water-tight means. For instance, the conduit 107 may be terminated with a needle 504, extending from the top surface of the core cylinder, which is engaged with a rubber disk 505, located on the bottom face of disk 501.

Figure 6:
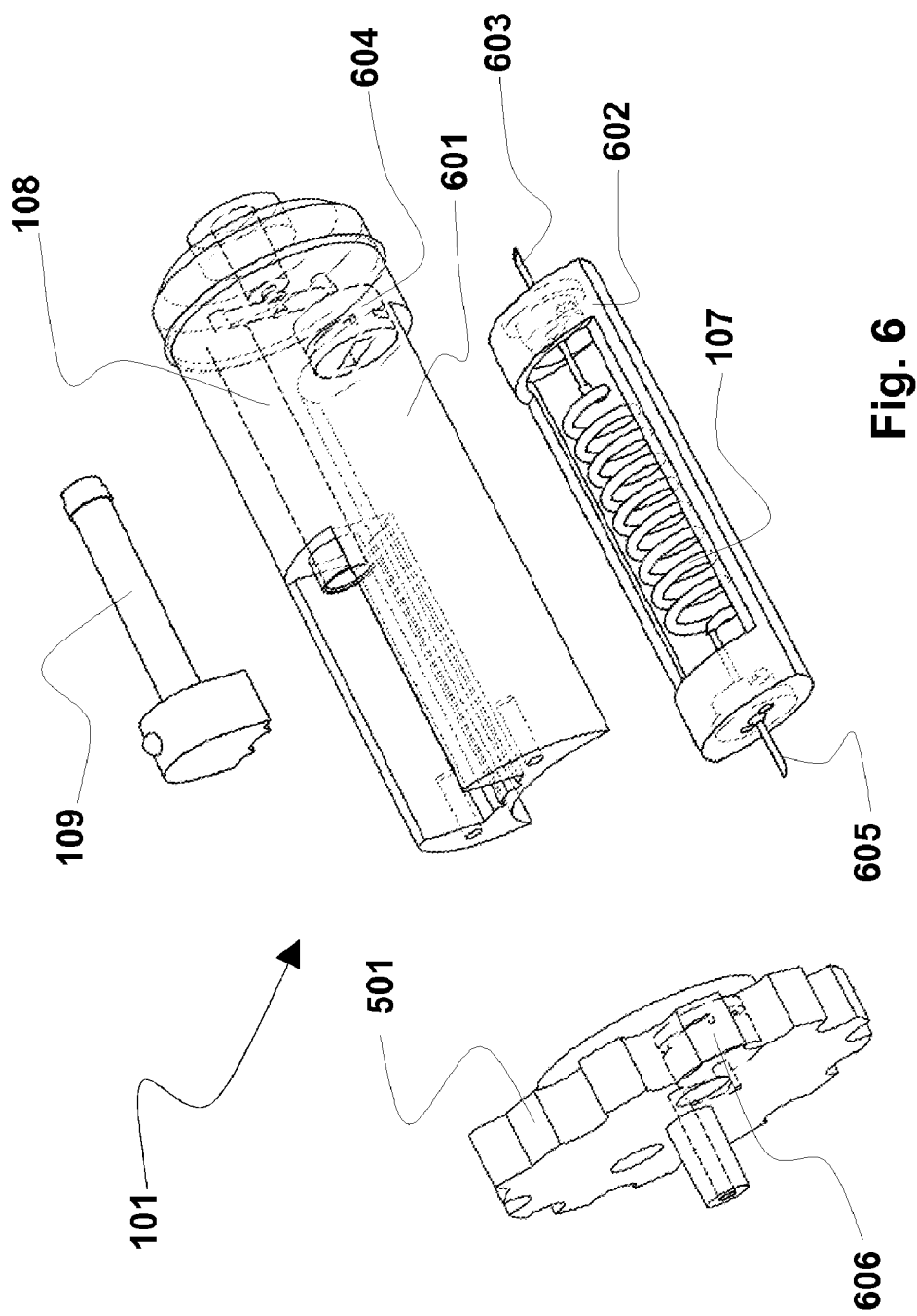
FIG. 6 represents an exploded view of an embodiment of the core cylinder of a device according to the invention.

Whilst the core cylinder has been illustrated above as a single element, or as a combination of two elements according to the embodiment of FIG. 5, it may be advantageous to build up the core cylinder of different detached pieces. For instance, as illustrated in FIG. 6, representing an exploded view of an embodiment of the invention, the core cylinder may comprise a support body 601 comprising the reservoir 108, through which the respective plunger 109 is allowed to run. The conduit 107 is provided in a separate piece 602, which engages with support body 601 through water-tight connecting means (e.g. needle 603 cooperating with rubber disk 604), to connect conduit 107 with proximal end's passage 103b. The opposite end of piece 602 has corresponding water-tight connecting means (e.g. a second needle 605 cooperating with a second rubber disk 606 positioned in retaining disk 501) to allow fluid communication between conduit 107 and disk 501.

The external cylinder can advantageously be provided with a graduated scale on the outer surface thereof, e.g. in the form of indices or marks disposed at regular intervals around the outer surface of the external cylinder. The indices or marks may be provided for instance in the form of colored lines or of protrusions, or of a combination of the two, preferably in combination with numbers indicating the volume of liquid introduced into conduit 107. The graduated scale is dimensioned so that each portion of relative turn of the external cylinder with respect to the core cylinder corresponds to a respective longitudinal movement of the piston 109 and thus to a corresponding volume of liquid introduced into or released from reservoir 108. For instance, the groove on the inner surface of the external cylinder and the reservoir 108 may be dimensioned so that $1/12$ of turn of the external cylinder with respect to the core cylinder (rotation angle of 30°) corresponds to a volume of about 20 µl. A mark can advantageously be provided on the peripheral surface of retaining disks 401 or 501 (e.g. a protrusion 404 or 506 as illustrated in FIG. 4 or 5, or a colored dot), in order to determine the relative degree of rotation of the external cylinder with respect to the core cylinder.

To better control the relative rotation of the cylinders, cooperating means are preferably provided on the two cylinders to allow a stepwise or discrete rotation of the external cylinder with respect to the core cylinder. Preferably, said cooperating means include a plurality of cavities or grooves disposed, preferably at regular intervals, on the external cylinder (e.g. in correspondence with the indices of the graduated scale illustrated above), said cavity or grooves cooperating with retractable protruding means (e.g. a small ball or cylinder cooperating with a resilient means) disposed on the core cylinder. According to an embodiment, a series of cavities or grooves can be provided at regular intervals around the inner longitudinal surface of the external cylinder, while retractable protruding means is provided on the longitudinal surface of the core cylinder. Said protruding means can advantageously be in the form of a ball (or of a smoothened cylinder), moving within and along a seat disposed radially on the external surface of the core cylinder; the ball is kept in contact with the inner surface of the external cylinder by means of resilient means (e.g. a metallic or plastic spring) positioned in the radial cavity, behind the ball, and pushing the ball toward said inner surface. Alternatively, the grooves or cavities can be provided on the longitudinal surface of the core cylinder, while the retractable protruding means is provided on the internal surface of the external cylinder. Alternatively, retractable protruding means can be inserted in the peripheral part of the bottom surface of distal disk 401 or 501 (i.e. the surface in contact with core cylinder 101) while corresponding cavities are provided on the rim of distal end 106 of the external cylinder. Similarly, protruding means can be disposed in the rim of the external cylinder, while corresponding grooves or cavities are provided on the peripheral part of the bottom surface of the distal disk.

The provision of indices on the surface of the cylinders, preferably in combination with the stepwise or discrete relative rotation of the two cylinders, allows an extremely accurate determination of very small volumes of liquid to be withdrawn within the conduit 107 of the device 100.

The device and its components can be made of any material suitable for medical applications, which can be selected according to the specific form and function of each component. For instance, most components of the device can be made of suitable rigid plastic materials (e.g. moldable resin). On the other hand, conduit 107 can advantageously be made of a soft plastic material (e.g. a thermoformable polyethylene tubing). Alternatively, conduit 107 can be formed by joining two molded halves, each of them being provided with a respective mirror-like tortuous groove on the face to be joined, the joining of the two parts thus forming the desired conduit. Similarly, conventional water-tight connecting means can be employed for those parts and components of the device where water-tight fluid communication is required. Water-tight connecting means include, for instance, rubber water-tight stoppers in combination with metal needles, barbed fittings in combination with soft plastic (e.g. polyethylene) tubing, compression fitting with nuts (e.g. Swagelok, Solon Ohio, USA) for holding soft plastic tubing or small luer-like male-female connections.

Figure 7:
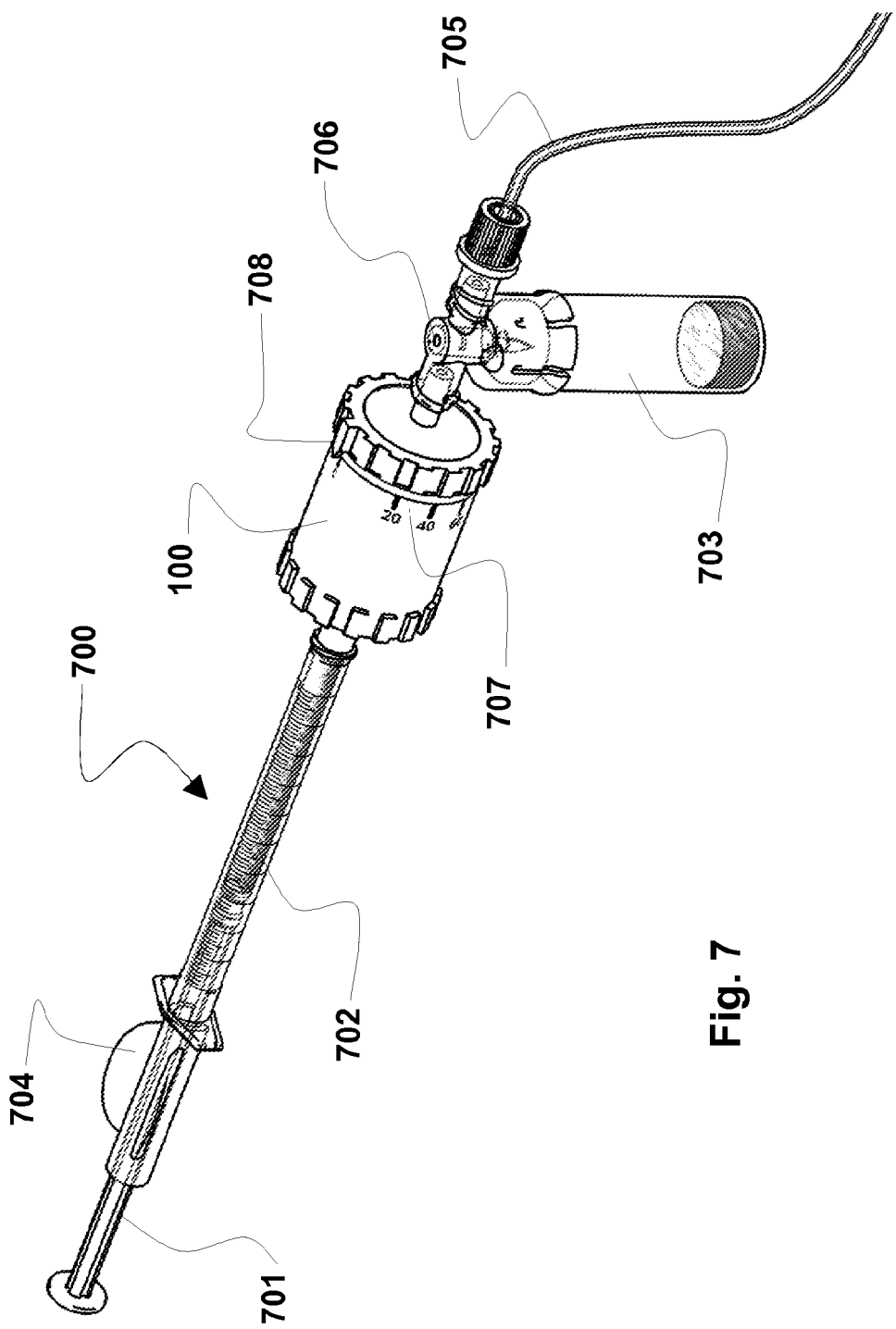
FIG. 7 represents an administration setup using the device of the invention.

The device of the invention may be operated in the following manner, illustrated in schematic FIG. 7. A syringe 700 (e.g. a prefilled syringe containing for instance saline) with a plunger 701 and a reservoir 702 is connected to the proximal end of the device 100. The device 100 (and, if necessary, the administration means 705 connected to the distal end of the device) is first flushed with a portion of the liquid contained in the syringe and then the distal end of the device is connected to a vial 703 containing a liquid preparation of a pharmaceutical agent. By rotating the external cylinder of the device, the desired volume of preparation is withdrawn from the vial and introduced into the conduit 107 (not shown) of the device. The exact volume of liquid to be withdrawn into conduit 107 is accurately determined by means of graduated scale 707 (disposed on the external cylinder), cooperating with mark 708 (on the peripheral surface of the distal disk of the core cylinder). Advantageously, the graduated scale is dimensioned so to take into account any dead volume of saline which needs to be withdrawn before the actual withdrawal of the pharmaceutical preparation. With reference to FIG. 7, this dead volume corresponds for instance to the tubing inside the vial 703 up to the connection with the three-way valve 706.

Means are preferably provided in the system to avoid withdrawal of saline from the syringe during rotation of the device. For instance, the plunger of the syringe 700 is blocked by inserting blocking means 704 between the plunger's head and the upper surface of the syringe's reservoir. Suitable blocking means may be for instance a cylindrical U-shaped plastic stopper which can be clipped on the plunger. The stopper 704 may advantageously be inserted onto the plunger before the initial flushing of saline and may have a length such as to allow the ejection of a predetermined amount of liquid before stopping the plunger. Alternatively, to avoid undesired withdrawal of saline from the syringe during rotation of the device, a pressure activated/pressure relief valve (e.g. Halkey-Roberts St. Petersburg Fla., USA) is inserted between the syringe and device 100. Said valve remains closed when the pressure is below a certain cracking value (typically 50 to 500 mbar); when the preparation is withdrawn into conduit 107, the pressure drop is not enough to open the valve, thus avoiding the saline withdrawal from the syringe. On the other hand, during bolus injection, the pressure applied by the syringe's plunger on the saline is sufficient to open the valve and let the saline flow through conduit 107 and then out of device 100.

Once the desired volume of preparation has been withdrawn from the vial, the vial is disconnected and the distal end of the device 100 is connected to administration means 705 (e.g. a tubing ending with an injection needle); by pushing the plunger 701, the preparation of pharmaceutical agent contained in conduit 107 is thus administered as a bolus, followed by the remaining saline contained in the syringe's reservoir 702. Preferably, the device 100 is connected to a three-way valve 706 (e.g. Mixject®, West Pharmaceutical GmbH, Germany), which can be alternatively connected to the vial containing the preparation of pharmaceutical agent or to the administration means. In a preferred embodiment of the invention, a portion of the volume of saline contained in the syringe 700 can be used to reconstitute a dry residue contained in the vial. Thus, after flushing a first volume of saline through administration means 705, the three-way valve is switched to connect the syringe with the vial and the desired volume of saline is injected into the vial for reconstituting the residue, with optional agitation of the vial for reconstituting the preparation. Then, the desired volume of liquid preparation is withdrawn from the vial (which can be optionally turned upside-down to facilitate the operation) by rotating the device 100, and finally the three-way valve is switched back to connect the syringe with administration means, to allow administration of the bolus preparation. Administration means include any suitable administration device such as, for instance a catheter optionally connected to a soft plastic tubing.

According to a preferred embodiment, the vial contains a lyophilized dry residue in contact with a gas which, upon reconstitution with saline, forms an aqueous suspension of gas-filled microvesicles suitable for ultrasound imaging. Examples of suitable suspensions of gas-filled microvesicles, of respective reconstitutable residues in contact with a gas and preparations thereof, are disclosed for instance in U.S. Pat. Nos. 5,271,928, 5,413,774, 5,827,504, 5,597,549, WO 04/069284, U.S. Pat. Nos. 5,711,933 or 6,333,021. For instance, the device can advantageously be employed for the bolus administration of Sonovue® (Bracco International BV).

The invention claimed is:

1. A device for transferring a volume of a pharmaceutical suspension, said device comprising:
   a) an external cylinder, comprising:
      i) an inner and an outer longitudinal surface, said inner surface comprising guiding means; and
      ii) a proximal end and a distal end;
   b) a core cylinder, comprising:
      i) a respective inner and outer longitudinal surface;
      ii) a proximal end and a distal end, said proximal and distal ends comprising respective passages, said passages being in fluid communication with corresponding connecting means adapted to connect the device with respective means for injection:

iii) a conduit, arranged between and in fluid communication with respective passages at the proximal and distal ends of the core cylinder; and iv) a cylindrical reservoir, in fluid communication with said passage at the proximal end of the core cylinder and cooperating with a respective plunger, said plunger being adapted to operatively engage with the guiding means;

said plunger and said guiding means being operatively engaged such that a relative rotation of the external cylinder with respect to the core cylinder results in a corresponding longitudinal movement of the plunger along the reservoir.

2. The device according to claim 1, wherein said guiding means comprises a helicoidal groove.

3. The device according to claim 2, wherein the plunger comprises a head provided with a protrusion adapted to engage with said helicoidal groove.

4. The device according to claim 1, wherein the core cylinder and the external cylinder are provided with respective blocking means which cooperate to substantially avoid longitudinal movements of the core cylinder with respect to the external cylinder.

5. The device according to claim 4 wherein said blocking means comprise cooperating portions at respective proximal ends of the core cylinder and of the external cylinder, respectively.

6. The device according to claim 5, wherein said blocking means further comprise retaining means connected to the distal end of the core cylinder.

7. The device according to claim 6 wherein said retaining means form part of the core cylinder.

8. The device according to claim 1, wherein the external cylinder is provided with a graduated scale on the outer surface thereof.

9. The device according to claim 8 wherein said graduated scale is in the form of indices disposed at regular intervals around the outer surface of the external cylinder.

10. The device according to any one of claims 1 or 8, wherein the core cylinder and the external cylinder further comprise respective cooperating means resulting in a stepwise or discrete rotation of the external cylinder with respect to the core cylinder.

11. The device according to claim 10 wherein said cooperating means comprise:

a) a plurality of cavities or grooves provided on the surface of the external cylinder; and b) retractable protruding means provided on the surface of the core cylinder and cooperating with said cavities or grooves.

12. A system for administering a preparation of a pharmaceutical compound to a patient comprising a syringe, a device according to any one of claims 1 or 8, and administration means.

13. The system according to claim 12 further comprising a vial containing a pharmaceutical agent and a three-way valve.

14. The system according to claim 13 wherein said pharmaceutical agent is an aqueous suspension of gas-filled microvesicles.

* * * * *